United States Patent [19]

Zimmerman et al.

[11] Patent Number: 5,702,697

[45] Date of Patent: Dec. 30, 1997

[54] TREATMENT FOR BIOLOGICAL DAMAGE USING A COLONY STIMULATING FACTOR AND A BIOLOGICAL MODIFIER

[75] Inventors: Robert Zimmerman, Lafayette; Benedict J. Marafino, Jr., San Francisco, both of Calif.

[73] Assignee: Chiron Corporation, Emeryville, Calif.

[21] Appl. No.: 457,629

[22] Filed: Jun. 1, 1995

Related U.S. Application Data

[63] Continuation of Ser. No. 289,844, Aug. 12, 1994, Pat. No. 5,508,031, which is a continuation of Ser. No. 49,070, Apr. 16, 1993, abandoned, which is a continuation of Ser. No. 626,975, Dec. 12, 1990, abandoned, which is a division of Ser. No. 399,386, Aug. 25, 1989, Pat. No. 4,985,241, which is a continuation of Ser. No. 113,643, Oct. 26, 1987, abandoned, which is a continuation-in-part of Ser. No. 933,475, Nov. 21, 1986, abandoned.

[51] Int. Cl.$^6$ .......................... A61K 38/19; C07K 14/53
[52] U.S. Cl. .......................... 424/85.1; 530/351; 514/2; 514/8; 514/885
[58] Field of Search ................ 424/85.1, 85.2; 530/351; 514/2, 8, 885

[56] References Cited

U.S. PATENT DOCUMENTS

| | | | |
|---|---|---|---|
| 4,645,830 | 2/1987 | Yasushi et al. | 530/351 |
| 4,677,064 | 6/1987 | Mark et al. | 435/68 |
| 4,762,705 | 8/1988 | Rubin | 424/85.1 |
| 4,962,091 | 10/1990 | Eppstein et al. | 514/2 |
| 4,980,160 | 12/1990 | Goldberg et al. | 424/85.1 |
| 4,985,241 | 1/1991 | Zimmerman et al. | 424/85.1 |
| 5,002,879 | 3/1991 | Bowlin et al. | 435/71.1 |
| 5,021,239 | 6/1991 | Garnick | 424/85.1 |
| 5,508,031 | 4/1996 | Zimmerman et al. | 424/85.2 |

FOREIGN PATENT DOCUMENTS

| | | |
|---|---|---|
| 0 078 434 | 5/1983 | European Pat. Off. . |
| 0 158 487 | 10/1985 | European Pat. Off. . |
| 62-263127 | 11/1987 | Japan . |
| 1-500905 | 3/1989 | Japan . |
| 1 526 205 | 9/1978 | United Kingdom . |
| WO 88/02632 | 4/1988 | WIPO . |
| WO 94/14473 | 7/1994 | WIPO . |

OTHER PUBLICATIONS

Braun et al., "The In Vitro Development of Cytotoxicity In Response To Granulocyte/Macrophage–Colony–Stimulating Factor or Interferon γ in the Peripheral Blood Monocytes of Patients With Solid Tumors: Modulation by Arachidonic Acid Metabolic Inhibitors," *Cancer Immunol. Immunother.*, 32:55–61 (1990).

Dayer et al., "Cachectin/Tumor Necrosis Factor Stimulates Collagenase and Prostaglandin $E_2$ Production by Human Synovial Cells and Dermal Fibroblasts," *J. Exp. Med.*, 162:2163–2168 (Dec., 1985).

Delemarre et al., "Granulocyte–Macrophage Colony–stimulating Factor (GM–CSF) Reduces Toxoplasmastatic Activity of Human Monocytes Via Induction of Prostaglandin $E_2$ ($PGE_2$)," *Clin. Exp. Immunol.*, 102:425–429 (1995).

Desai et al., "Killing of *Histoplasma capsulatum* by Macrophage Colony Stimulating Factor–Treated Human Monocyte–Derived Macrophages: Role for Reactive Oxygen Intermediates," *J. Med. Microbiol.*, 43:224–229 (1995).

Dinarello et al., "Tumor Necrosis Factor (Cachectin) is an Endogenous Pyrogen and Induces Production of Interleukin 1," *J. Exp. Med.*, 163:1433–1450 (Jun., 1986).

Kharazmi et al., "Modulation of Human Neutrophil and Monocyte Chemotaxis and Superoxide Responses by Recombinant TNF–Alpha and GM–CSF," *Immunobiol.*, 177:363–370 (1988).

Kitagawa et al., "The Respiratory Burst of Granulocytes: Modulation by Inflammatory Mediators and Its Mechanism," *Tokai J. Exp. Clin. Med.*, 13(6):299–305 (1988).

Maeda et al., "Enhanced Antitumor Effect of Recombinant Human Tumor Necrosis Factor in Combination with Recombinant Human Granulocyte Colony–stimulating Factor in BALB/c Mice," *Jpn. J. Cancer Res.*, 84:921–927 (Aug., 1993).

Ohsaka et al., "Effects of Granulocyte Colony–Stimulating Factor and Granulocyte–Macrophage Colony–Stimulating Factor on Respiratory Burst Activity of Neutrophils in Patients With Myelodysplastic Syndromes," *Clin. Exp. Immunol.*, 91:308–313 (1993).

Palladino et al., "Tumor Necrosis Factor–Alpha and Interferon–Gamma Induce Neutrophils From Normal and Chronic Granulomatous Disease Patients to Release Superoxide," *Ped. Res.*, 20:302A (1986) (Abstract).

Random House Webster's College Dictionary, Random House, Inc., New York, p. 747 (1992).

Whicher et al., "Cytokines in Disease," *Clin. Chem.*, 36(7):1269–1281 (1990).

Yuo et al., "Tyrosine Phosphorylation and Intracellular Alkalinization Are Early Events in Human Neutrophils Stimulated by Tumor Necrosis Factor, Granulocyte–Macrophage Colony–Stimulating Factor and Granulocyte Colony–Stimulating Factor," *Biochim. et Biophys. Acta*, 1156:197–203 (1993).

Adams et al., "Plasma Glutathione and Glutathione Disulfide in the Rat: Regulation and Response to Oxidative Stress," *J. Pharmacol. Exp. Ther.*, 227(3):749–754 (1983).

Alexander et al., "Synergistic Enhancement by Tumor Necrosis Factor of in Vitro Cytotoxicity from Chemotherapeutic Drugs Targeted at DNA Topisomerase II," *Cancer Research*, 47:2403–2406 (May 1, 1987).

(List continued on next page.)

*Primary Examiner*—John Ulm
*Assistant Examiner*—Prema Mertz
*Attorney, Agent, or Firm*—David A. Gass; Paul B. Savereide; Robert P. Blackburn

[57] ABSTRACT

Damage to cells, tissue and other body parts in a mammalian host may be treated by using a colony stimulating factor in conjunction with at least one biological modifier, which may be a free radical scavenger or a metabolic inhibitor. The biological modifier is preferably uric acid, buthionine sulphoximine, vitamin C, aspirin, or nordihydroguaiaretic acid. Such a combination may be used to treat, for example, cancer, infectious diseases, and damage caused by radiation therapy, high oxygen tension, and chemotherapy.

32 Claims, No Drawings

OTHER PUBLICATIONS

Almqvist et al., "Treatment of Experimental Canine Endotoxin Shock with Ibuprofen, a Cyclooxygenase Inhibitor," *Circulatory Shock*, 13:227–232 (1984).

Ames et al., "Uric acid provides an antioxidant defense in humans against oxidant–and readical–caused aging and cancer: A hypothesis," *PNAS (USA)*, 78(11):6858–6862 (Nov., 1981).

Andrews et al., "Differential Potentiation of Alkylating and Platinating Agent Cytotoxicity in Human Ovarian Carcinoma Cells by Glutathione Depletion," *Cancer Res.*, 45:6250–6253 (Dec., 1985).

Aoki et al., "Indomethacin Augments Inhibitory Effect of Interferons on Lymphoproliferative Response," *Immunology Letters*, 7:321–24 (1984).

Arrick et al., "Inhibition of Glutathione Synthesis Augments Lysis of Murine Tumor Cells by Sulfhydryl–reactive Antineoplastics," *J. Clin. Invest.*, 71(2):258–267 (Feb., 1983).

Aune and Pogue, "Inhibition of Tumor Cell Growth by Interferon–$\gamma$ is Mediated by Two Distinct Mechanisms Dependent upon Oxygen Tension: Induction of Tryptophan Degradation and Depletion of Intracellular Nicotinamide Adenine Dinucleotide", *J. Clin. Invest.*, 84:863–875 (Sep., 1989).

Bachwich et al., "Tumor Necrosis Factor Stimulates Interleukin–1 and Prostaglandin $E_2$ Production in Resting Macrophages," *Biochemical and Biophysical Research Communications*, 136:94–101 (1986).

Badwey and Karnovsky, "Active Oxygen Species And The Functions Of Phagocytic Leukocytes," *Ann. Rev. Biochem.*, 49:695–726 (1980).

Balkwill et al., "Human Tumor Xenografts Treated with Recombinant Human Tumor Necrosis Factor Alone or in Combination with Interferons," *Cancer Research*, 46:3990–3993 (1986).

Bollag, "Retinoids and Interferon: a new promising combination?" *British J. of Haematol.*, 79(Suppl. 1):87–91 (1991).

Borden, et al., "Lymphokines and Cytokines as Cancer Treatment Immunotherapy Realized," *Cancer* (Supplement), 65(3):800–814 (Feb. 1, 1990).

Bus and Gibson, "Lipid Peroxidation And Its Role In Toxicology," *Rev. Biochm. Toxicol.*, (Hodgson et al., Eds.)., Elsevier, North Holland, pp. 125–149 (1979).

Cerutti et al., "Membrane–Mediated Chromosomal Damage," *Genes And Proteins In Oncogenesis*, (Academic Press, NY)., pp. 55–67 (1983).

Chun et al., "Enhancement of Cytotoxic Activity of Natural Killer Cells by Interleukin 2, and Antagonism between Interleukin 2 and Adenosine Cyclic Monophosphate," *Scand. J. Immunol.* 22:375–81 (1985).

Clark, et al., "Tumor Necrosis Factor and Reactive Oxygen Species: Implications for Free Radical–Induced Tissue Injury," *Upjon Symposium/Oxygen Radicals*, 122–129 (Apr. 1987).

Crook et al., "Glutathione Depletion as a Determinant of Sensitivity of Human Leukemia Cells to Cyclophosphamide," *Cancer Res.*, 46:5035–5038 (1986).

Das et al., "Free Radicals as Possible Mediators of the Actions of Interferon," *J. Free Radicals in Biology and Medicine*, 2:183–188 (1986).

DiGuiseppi et al., "The Toxicology Of Molecular Oxygen," *CRC Crit. Rev. Toxicol.*, 12:315–342 (1984).

Dorr et al., "Cytotoxic effects of glutathione synthesis inhibition by L–buthionine–(SR)–sulfoximine on human and murine tumor cells," *Invest. New Drugs*, 4:305–313 (1986).

Dreno et al., "The treatment of 45 patients with cutaneous T–cell lymphoma with low doses of Interferon–$\alpha$2a and etretinate," *British J. of Dermatol.*, 125:456–459 (1991).

Ferrante, "Tumor Necrosis Factor Alpha Potentiates Neutrophil Antimicrobial Activity: Increased Fungicidal Activity against *Torulopsis glabrata* and *Candida albicans* and Associated Increases in Oxygen Radical Production and Lysosomal Enzyme Release," *Infect. Immunity*, 57(7):2115–212 2(Jul., 1989).

Freund and Pick, "The Mechanism of Action of Lymphokines IX. The Enzymatic Basis of Hydrogen Peroxide Production by Lymphokine–Activated Macrophages," *J. Immunol.*, 137(4):1312–1318 (Aug. 15, 1986).

Fridovich, "The Biology of Oxygen Radicals," *Science*, 201:875–880 (1978).

Front et al., "Administered Dose and Tumor Dose of Bleomycin Labeled with Cobalt–57 in Mice and Men," *J. Nuclear Med.*, 31(11):1784–1790 (Nov., 1990).

Gerberick et al., "Relationship Between Pulmonary Inflammation, Plasma Transudation, and Oxygen Metabolite Secretion by Alveolar Macrophages," *J. Immunol.*, 137(1):114–121 (Jul. 1, 1986).

Ghezzi et al., "Role of Reactive Oxygen Intermediates in the Interferon–mediated Depression of Hepatic Drug Metabolism and Protective Effect of N–Acetylcysteine in Mice," *Cancer Res.* 45:3444–3447 (Aug., 1985).

Godal et al., "Pharmacological studies of ricin in mice and humans," *Cancer Chemother. Pharmacol.*, 13:157–163 (1984).

Green et al., "Potentiation of Melphalan Cytotoxicity in Human Ovarian Cancer Cell Lines by Glutathione Depletion," *Cancer Res.*, 44:5427–5431 (1984).

Hamilton et al., "Augmentation of Adriamycin, Melphalan, and Cisplatin Cytotoxicity in Drug–Resistant and Sensitive Human Ovarian Carcinoma Cell Lines by Buthionine Sulfoximine Mediated Glutathione Depletion," *Biochem. Pharmacol.*, 34(14):2583–2586 (Jul., 1985).

Hauser et al., "Manipulation of Oxygen Radical–scavenging Capacity in Mice Alters Host Sensitivity to Tumor Necrosis Factor Toxicity but Does Not Interfere with Its Antitumor Efficacy," *Cancer Res.*, 50:3503–3508 (Jun. 15, 1990).

Hill et al., "Granulocyte–macrophage colony–stimulating factor inhibits tumor growth," *Br. J. Surg.*, 80:1543–1546 (Dec., 1993).

Hird, "Immunotherapy with Monoclonal Antibodies," in *Genes and Cancer*, D. Carney & K. Sikora, Eds., New York: John Wiley & Sons (1990), pp. 183–189.

Hodgkiss and Middleton, "Effects of Glutathione Depletion Using Buthionine Sulphoximine on the Cytotoxicity of Nitroaramoatic Compounds in Mammalian Cells In Vitro," *Biochem. Pharmacol.*, 34:2175–2178 (1985).

Itri, "The Interferons," *Cancer* (Supplement), 70(4):940–945 (Aug. 15, 1992).

Iwasaka et al., "Antitumor Effects of Human Recombinant Interferon–$\gamma$ and Tumor Necrosis Factor On Five Cervical Adenocarcinoma Cell Lines, in Vivo and in Vitro," *Gynecologic Oncology*, 42:39–43 (1991).

Jiang et al., "Potentiation of IL–2–Induced T–Cell Proliferation by Retinoids," *Int. J. Immunopharmac.*, 14(2):195–204 (1992).

Johnston, "The Production of Superoxide by Cultured Macrophages," in *CRC Handbook of Methods for Oxygen Radical Research*, pp. 373–377 (1982).

Jones, "Free Radicals in Immunological Killing: The Case of Tumor Necrotising Factor (TNF)", *Med. Hypotheses* 21(3):267–271 (1986).

Kawakami et al., "Cachetin/TNF as well as Interleukin–1 Induces Prostacyclin Synthesis in Cultures Vascular Endothelial Cells," *Biochemical and Biophysical Research Communications*, 141:482–487 (1986).

Kimbro and Taylor, "TNF Resistance Correlates to Free Radical Resistance," a *Molecular and Cellular Biology of Cytokines*, pp. 227–232 (Wiley–Liss, Inc.) (1990).

Konno et al., "Effect of Liposomal Interleukin–2 on Ascites–Forming Rat Hepatoma," *J. Surg. Oncol.*, 51:33–37 (1992).

Krosnick et al., "Studies of the mechanisms of toxicity of the administration of recombinant tumor necrosis factor α in normal and tumor–bearing mice," *Cancer Immunol. Immunother.*, 30:133–138 (1989).

Kull and Cuatrecasas, "Possible Requirement of Internalization in the Mechanism of in Vitro Cytoxicity in Tumor Necrosis Serum," *Cancer Research*, 41:1885–4890 (Dec., 1981).

Kunkel et al., "Regulation of Macrophage Tumor Necrosis Factor Production by Prostaglandin $E_2$," *Biochemical and Biophysical Research Communications*, 137(1):404–410 (May 29, 1986).

Larrick et al., "Recombinant Tumor Necrosis Factor Causes Activation of Human Granulocytes," *Blood*, 69(2):640–644 (Feb., 1987).

Lesko et al., "Role of Superoxide in Deoxyribonucleic Acid Strand Scission," *Biochemistry*, 19:3023–3028 (1980).

Liang et al., "Regulation by glutathione of interleukin–4 activity on cytotoxic T cells," *Immunology*, 75:435–440 (1992).

Malik et al., "Antitumor Activity of γ–Interferon in ascitic and Solid Tumor Models of Human Ovarian Cancer," *Cancer Res.*, 51:6643–6649 (Dec. 15, 1991).

Marcus et al., "Serve Hypovitaminosis C Occurring as the Result of Adoptive Immunotherapy with High–Dose Interleukin 2 and Lymphokine–activated Killer Cells," *Cancer Research*, 47:4028–4212 (Aug. 1, 1987).

Martin et al., "Role of Murine Tumor Models in Cancer Research," *Cancer Res.*, 46:2189–2192 (Apr., 1986).

Mavier and Edginton, "Human Monocyte–Mediated Tumor Cytotoxicity I, Demonstration on an Oxygen–Dependent Myeloperoxidase–Independent Mechanism," *J. Immunol.*, 132(4):1980–1986 (Apr., 1984).

McDonald and Georgouras, "Treatment of Basal Cell Carcinoma with Intralesional Interferon Alpha: A Case Report and Literature Review," *Australs J. Dermatol.*, 33:81–86 (1992).

Meister and Anderson, "Glutathione," *Ann. Rev Biochem.*, 52:711–760 (1983).

Minchinton et al., "Glutathione Depletion in Tissues After Administration of Buthionine Sulphoximine," *Int. J. Radiation Oncology Biol. Phys.*, 10:1261–1264 (1984).

Moody and Hassan, "Mutagenicity of oxygen free radicals," *PNAS (USA)*, 79:2855–2859 (May, 1982).

Morin and Ballet, "A recent overview on in vitro and in vivo immunological activities of methisoprinol," *Allergol. Immunopathol.*, 10(2):109–114 (1982).

Neta et al., "Interleukin 1 Is A Radioprotector," *J. Immunol.*, 136(7):2483–2485 (Apr., 1986).

Novi, "Regression of a Platoxin $B_1$–Induced Hepatocellular Carcinomas by Reduced Glutathione,"0 *Science* 212:541–542 (May, 1981).

Ochoa et al., "Increased Circulating Nitrogen Oxides After Human Tumor Immunotherapy: Correlation With Toxic Hemodynamic Changes," *J. Natl. Cancer Inst.* 84(11):864–867 (Jun. 3, 1992).

Ono et al., "Combined effect of buthionine sulfoximine and cyclophosphamide upon murine tumours and bone marrow," *Br. J. Cancer (UK).*, 54:749–754 (1986).

Ozols, "Pharmacologic Reversal of Drug Resistance in Ovarian Cancer," *Semin. Oncol. Suppl.* 12(3):7–11 (Sep., 1985).

Ozols et al., "Glutathione Depletion With Buthionine Sulfoximine: Potential Clinical Applications," *Devel. Oncol.*, 47:277–293 (1986).

Palladino et al., "γ–Irradiation–induced mortality: protective effect of protease inhibitors in chickens and mice," *Int. J. Radiat. Biol.*, 41(2):183–191 (1982).

Palladino et al., "Tumor Necrosis Factor–Alpha And Interferon–Gamma Induce Neutrophils From Normal And Chronic Granulomatous Disease Patients To Release Superoxide," *Clin. Res.*, 34(2):502 (Abstract Only)(1986).

Petkau, "Radiation carcinogenesis from a membrane perspective," *Acta. Physiol. Scand. (Suppl.)*, 492:81–90 (1980).

Ralph et al., "Biological Properties and Molecular Biology of the Human Macrophage Growth Factor, CSF–1," *Immunobiol.* 172:194–204 (1986).

Romine and Kessel, "Intracellular Glutathione as a Determinant of Responsiveness to Antitumor Drugs," *Biochem. Phrmacol. (UK).*, 35(19):3323–3326 (1986).

Rose, "Evaluation of Plantinol Analogs Using the M5076 Murine Sarcoma," *Anticancer Res.*, 6:577–562 (1986).

Rosen, "The Synergism of γ–Interferon and Tumor Necrosis Factor in Whole Body Hyperthermia With Vitamin C to Control Toxicity," *Med. Hypotheses*, 38:257–258 (1992).

Ruff and Gifford, "Rabbit Tumor Necrosis Factor: Mechanism of Action," *Infection and Immunity*, 31(1):380–385 (Jan., 1981).

Russo et al., "Selective Modulation of Glutathione Levels in Human Normal versus Tumor Cells and Subsequent Differential Response to Chemotherapy Drugs," *Cancer Res.*, 46:2845–2848 (Jun., 1986).

Russo et al., "The Roles Of Intracellular Glutathione In Antineoplastic Chemotherapy," *Int. J. Radiat. Oncol. Biol. Phys.*, 12:1347–1354 (1986).

Slater, "Free–radical mechanisms in tissue injury," *Biochem. J.*, 222:1–15 (1984).

Somfai–Relle et al., "Reduction in cellular glutathione by buthionine sulfoximine and sensitization of murine tumor cells resistant to L–phenylalanine mustard," *Biochem. Pharmacol.*, 33(3):3485–490 (1984).

Strander, "Clinical Effects of Interferon Therapy with Special Emphasis on Antitumor Efficacy," *Acta Oncologia*, 28:355–362 (1989).

Svedersky, "Enhanced Antitumor Activity Of Recombinant IFN–Gamma In Combination with Tumor Necrosis Factors And Chemotherapeutic Agents," *Int. J. of Immunopharm.*, 7(3):330 (Abstract) (1985).

Takano et al., "Regulatory Effect of Cytokines on Poly–Morphonuclear Leukocetes (PMNs)–Derived Superoxide Production," *Free Radical Biol. Med.*, 9(Suppl. 1):148, (Abstract #15.37) (1990).

Tew et al., "Relationship of Glutathione Depletion and Inhibition of Glutathione-S-Transferase Activity to the Antimitotic Properties of Estramustine," *Cancer Treatment Rep.*, 70(6):715–720 (Jun., 1986).

Thomassen et al., "Modulation of Human Alveolar Macrophage Tumoricidal Activity by Recombinant Macrophage Colony-Stimulating Factor," *J. Biol. Response Modifiers*, 9(1):87–91 (1990).

Thomassen et al., "Macrophage Colony Stimulating Factor Therapy: Effects on Monocytes," *Proc. Am. Assoc. Cancer Res. Annu. Meet.*, 32:268, (Abstract #1592) (Mar., 1991).

Tomasz, "$H_2O_2$ Generation During the Redox Cycle of Mitomycin C and DNA-Bound Mitomycin C," *Chem. Biol. Interact.*, 13:89–97 (1976).

Trissel, *Handbook of Injectable Drugs*, 5th Edition, American Society of Hospital Pharmacists (1988), p. 184.

Valeriote and Grates, "MOPC-315 Murine Plasmacytoma as a Model Anticancer Screen for Human Multiple Myeloma," *JNCI*, 76(1):61–65 (Jan., 1986).

Wang and Hanson, "Parenteral Formulations of Proteins and Peptides: Stability and Stabilizers,"0 *J. Parenteral Sci. Tech.*, (Suppl.), 42(2s):s1–s26 (1988).

Warren and Ralph, "Macrophage Growth Factor CSF-1 Stimulates Human Monocyte Production of Interferon, Tumor Necrosis Factor, and Colony Stimulating Activity," *J. Immunol.*, 137(7):2281–2285 (Oct. 1, 1986).

White et al., "Recombinant Tumor Necrosis Factor/Cachetin and Interleukin 1 Pretreatment Decreases Lung Oxidized Glutathione Accumulation, Lung Injury, and Morality in Rats Exposed to Hyperoxia," *J. Clin. Invest.*, 79:1868–1873 (Jun., 1987).

White and Ghezzi, "Protection against pulmonary oxygen toxicity by interleukin–1 and tumor necrosis factor: Role of antioxidant enzymes and effect of cyclooxygenase inhibitors," *Biotherapy*, 1:361–367 (1989).

Whloher and Evans, "Cytokines in Disease," *Clin. Chem*, 36(7):1269–1281 (1990).

Yamauchi et al., "Suppressive Effects of Intracellular Glutathione on Hydroxyl Radical Production Induced by Tumor Necrosis Factor," *Int. J. Cancer*, 46:884–888 (1990).

Zimmerman et al., "Oxidative Damage in Murine Tumor Cells Treated in Vitro by Recombinant Human Tumor Necrosis Factor," *Cancer Res.*, 49:1644–1648 (Apr. 1, 1989).

Zimmerman et al., "The Role of Oxidant Injury in Tumor Cell Sensitivity to Recombinant Human Tumor Necrosis Factor in Vivo Implications for Mechanisms of Action," *J. Immun.*, 142(4):1405–1409 (Feb. 15, 1989).

TREATMENT FOR BIOLOGICAL DAMAGE USING A COLONY STIMULATING FACTOR AND A BIOLOGICAL MODIFIER

The instant application is a continuation of U.S. patent application Ser. No. 08/289,844, filed Aug. 12, 1994, now U.S. Pat. No. 5,508,031; which is a continuation of U.S. patent application Ser. No. 08/049,070, filed Apr. 16, 1993, now abandoned; which is a continuation of U.S. patent application Ser. No. 07/626,975, filed Dec. 12, 1990, now abandoned; which is a Divisional of U.S. patent application Ser. No. 07/399,386, filed Aug. 25, 1989, now U.S. Pat. No. 4,985,241; which is a continuation of U.S. patent application Ser. No. 07/113,643, filed Oct. 26, 1987, now abandoned; which is a continuation-in-part of U.S. patent application Ser. No. 06/933,475, filed Nov. 21, 1986, now abandoned.

BACKGROUND OF THE INVENTION

This invention relates to a composition suitable for administration to mammalian hosts as a therapeutic formulation. More particularly, this invention relates to a combination therapy for free-radical bodily damage employing a lymphokine or cytotoxin such as tumor necrosis factor (TNF) and a biological modifier consisting of either one or more free radical scavengers that protect against damage caused by free-radical generation, or that selectively increase the susceptibility of a tumor to radical damage by depleting or reducing its radical scavenging capacity, or an inhibitor of one or both of the cyclooxygenase or lipoxygenase pathways of arachidonic acid metabolism.

Lymphokines and cytotoxins, such as interleukin-2, interferon-alpha, interferon-gamma, colony stimulating factor, and tumor necrosis factor, are proteins secreted by T cells and/or microphages upon activation by antigens or lectins. Interleukin-2 (IL-2), a lymphokine which is produced by normal peripheral blood lymphocytes and induces proliferation of antigen or mitogen stimulated T cells after exposure to plant lectins, antigens, or other stimuli, was first described by Morgan, D. A., et al., *Science* (1976) 193:1007–1008. Then called T cell growth factor because of its ability to induce proliferation of stimulated T lymphocytes, it is not recognized that in addition to its growth factor properties it modulates a variety of functions of immune system cells in vitro and in vivo and has been renamed interleukin-2 (IL-2). IL-2 is one of several lymphocyte-produced, messenger-regulatory molecules which mediate immunocyte interactions and functions.

Tumor necrosis factor (TNF) was first described by Carswell et al., *Proc. Natl. Acad. Sci. USA* (1975) 72:3666–3670 as an endotoxin-induced serum factor which causes necrosis of chemically transformed tumor cells when growing in mice. Human TNF is known to be cytotoxic to neoplastic cells, and has been produced in recombinant form. See Pennica et al., *Nature* (London) (1984) 312:724–729 and Shirai et al., *Nature* (London) (1985) 313:803–806, Wang et al., *Science* (1985) 228:149–154.

Interferons (IFN) constitute a group of naturally occurring proteins which are known to exhibit anti-viral, anti-tumor and immunoregulatory behavior. Two types of IFN have been identified based on differences in their observed biological properties and molecular structures: Type I and Type II. Beta-interferon (IFN-β) is a Type I IFN which can be induced in fibroblasts by viral challenge and contains about 165 amino acids. IFN-α is also a Type I IFN inducible in leukocytes, and IFN-γ is a Type II IFN which is induced in lymphocytes in response to specific mitogenic stimuli and contains 146 amino acids.

Combination chemotherapy using two or more anti-cancer drugs to treat malignant tumors in humans is currently in use in research and in the clinic. The anti-cancer drugs may be antimetabolites, alkylating agents, antibiotics, general poisons, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects to each drug.

For example, it is known that IL-2 may be used with IFN-γ to treat tumor-bearing hosts with synergistic results (European Patent Publication 149,551 published Jul. 24, 1985 (Genentech) and German Patent Publication 3411184 published Oct. 31, 1985 (Deut Roten Kreuzes)) or with augmentation of natural killer activity (Svedersky et al., *J. Immunol.* (1984), 133:714–718 and Shalaby et al., *J. Interferon Res.* (1985), 5:571–581). In addition, U.S. Statutory Invention Reg. No. H22, published Feb. 4, 1986 to Creasey et al., discloses a composition exhibiting a synergistic cytotoxic effect in combination therapy of certain breast cancer and myeloma cell lines using synergistically effective amounts of 5-fluorouracil and human recombinant beta-interferon. Furthermore, enhanced anti-tumor activity has been observed using IFN-γ in combination with TNF and chemotherapeutic agents. Svedersky et al., *Internl. J. of Immunopharm.* (1985) 7:330.

An understanding of the mechanisms of action of various lymphokines and cytotoxins and the basis of tumor cell sensitivity to such proteins would facilitate the clinical investigation and the design of clinical trials of these therapeutic agents. For example, TNF, which is produced primarily by macrophages, has shown an apparent selectivity for many tumor cells, but not normal cells, in its cytotoxic or cytostatic activities. See, e.g., Carswell et al., supra, Wang et al., supra, Ruff and Gifford in *Lymphokines, Volume 2*, ed. Pick, E. (Academic Press, Inc., NY, N.Y., 1981), pp. 235–272, Beutler and Cerami, *Nature* (1986) 320:584–588, and Urban et al., *Proc. Natl. Acad. Sci. USA* (1986) 83:5233–5237, and the references cited therein. The basis for this selective killing of tumor cells is known not to be due to receptor absence, inasmuch as $TNF^r$ cells, such as human diploid fibroblasts, have sufficient numbers of high affinity receptors, internalize TNF, and degrade it in an apparently similar fashion as $TNF^s$ cells do. Tsujimoto, M. et al., *Proc. Natl. Acad. Sci. USA* (1985) 82:7626–7630.

Interleukin-1 alone has a protective effect in a model of free radical dependent tissue injury. Neta et al., *J. Immunol.* (1986) 136:2483–2485. In addition, it has been found that TNF-α and IFN-γ induce neutrophils from normal and chronic granulomatous-disease patients to release superoxide. Palladino et al., *Clin. Res.* (1986) 34:502 and Palladino et al., *Ped. Res.* (1986) 20:302.

The biological activity of both oxygen-free radical species and related polyunsaturated fatty acid lipid peroxidation products has been well established. For example, the generation of reactive radical species has been found to be involved in the cytotoxic effects of ionizing radiation (see, e.g., Petkau, *Acta. Physiol. Scand. Suppl.* (1980) 492:81–90 and Biaglow et al., *Radiat. Res.* (1983) 95:437–455), various chemotherapeutic agents (see, e.g., Tomasz, *Chem. Biol. Interact.* (1976) 13:89–97, Lown and Sim, *Biochem. Biophys. Res. Commun.* (1977) 77:1150–1157 and Borek and Troll, *Proc. Natl. Acad. Sci. USA* (1983) 80:1304–1307), and a variety of other biological processes, including aging, and the initiation and promotion stages of experimental carcinogenesis (see, e.g., DiGuiseppi and Fridovich, *CRC Crit. Rev. Toxicol.* (1984) 12:315–342 and Slater, *Biochem.*

J. (1984) 222:1–15). The generation and release of reactive free radicals in the respiratory burst phenomenon used by various cells of the immune system is a well known mechanism of foreign target destruction. See, e.g., Bus and Gibson in *Rev. Biochem. Toxicol.*, eds. Hodgson et al. (Elsevier, North Holland, 1979), pp. 125–149 and Badwey and Karnovsky, *Ann. Rev. Biochem.* (1980) 49:695–726.

In aerobes, a variety of radical scavenging mechanisms have evolved at both the cellular and organismal level that confer protection from potentially lethal reactive oxygen species, such as the hydroxy radical, superoxide anion, and hydrogen peroxide. See, e.g., DiGuiseppi and Fridovich, supra, Slater, supra, and Bus and Gibson, supra. Importantly, oxygen radicals can initiate longer-lived chain reactions of lipid peroxidation that can be propagated from cell to cell. These peroxidation products are capable of damaging cellular DNA, RNA, protein, and cellular phospholipids. See, e.g., Slater, supra, Bus, supra, Moody and Hassan, *Proc. Natl. Acad. Sci. USA* (1982) 79:2855–2859, Lesko et al., *Biochemistry* (1980) 19:3023–3028, and Cerutti et al. in *Genes and Proteins in Oncogenesis* (Academic Press, NY, 1983), pp. 55–67. The protective cellular mechanisms against this kind of damage include anti-oxidants and radical scavengers in both the lipid (e.g., α-tocopherol, β-carotene) and aqueous (e.g., glutathione and ascorbic acid) phases of cells, as well as enzymes such as superoxide dismutase and catalase. See, e.g., Fridovich, *Science* (1978) 201:875–880 and Meister and Anderson, *Ann. Rev. Biochem.* (1983) 52:711–760. The high plasma uric acid level found in humans has also been shown to be a major radical protective factor. Ames et al., *Proc. Natl. Acad. Sci. USA* (1981) 78:6858–6862.

Glutathione (GSH) and related cellular sulfhydryl compounds represent one of the major mechanisms of detoxification of electrophilic metabolites of xenobiotics and oxygen/lipid radical species. Meister and Anderson, supra. Inhibition of free radicals is postulated as the way in which certain radioprotectors, such as the free radical scavengers cysteine and GSH, operate. GSH becomes oxidized to contain a dithio group as well as to protein-mixed disulfides, when cells are exposed to oxygen-generating compounds or other oxidative stresses. See Adams et al., *J. Pharmacol. Exp. Ther.* (1983) 227:749–754. Therefore, the content of oxidized GSH is one important indicator or either the type of damage to which a cell has been exposed or of its ability to protect itself from oxidative damage. Buthionine sulphoximine has been shown to be an inhibitor of GSH biosynthesis. See Minchinton et al., *Int. J. Radiation Oncology Biol. Phys.* (1984) 10:1261–1264.

A protein called monocyte cell line cytotoxin (MCCT) was characterized and the inhibitory effects of various protease inhibitors and hydrogen peroxide scavengers on MCCT activity were studies. Armstrong et al., *J.N.C.I.* (1985) 74:1–9. In addition, it was found that various hydroxyl radical scavengers inhibited production of a lymphotoxin. See Kobayashi et al., *J. Biochem.* (Tokyo) (1984) 95:1775–1782. Finally, methisoprinol, a purine derivative, has been shown to increase the production of lymphotoxin, which is a lymphokine. Morin and Ballet, *Allergol. Immunopathol.* (1982) 10:109–114.

Marcus et al., *Cancer Research*, 47:4208–4212 (1987) discloses use of vitamin C and IL-2.

Arrick et al., *J. Clin. Invest.*, 71:258–267 (1983) discloses that inhibition of glutathione synthesis (e.g., by buthionine sulfoximine (BSO)) enhances lysis of tumor cells by antineoplastic agents.

Romine and Kessel, *Biochem. Pharmacol.* (UK) (1986) 35:3323–3326 discloses the role of intracellular glutathione as a determinant of responsiveness to antitumor drugs.

Ono et al., *Br. J. Cancer* (UK) (1986) 54:749–754 discloses the combined effect of BSO and cyclophosphamide on murine tumors and bone marrow.

Hamilton et al., *Biochem. Pharmacol.* (Jul. 15, 1985) 34:2583–2586 discloses the enhancement of adriamycin, melphalen, and cisplatin cytotoxicity in drug-resistant and drug-sensitive carcinoma cell lines by use of BSO.

Andrews et al., *Cancer Res.* (Dec. 1985) 45:6250–6253 discloses the differential potentiation of alkylating and platinating agent cytotoxicity in human ovarian carcinoma cells by glutathione depletion.

Russo et al., *Cancer Res.* (June 1986) 46:2845–2848 discloses selective modulation of glutathione levels in human normal versus tumor cells and differential response to chemotherapy drugs.

Tew et al., *Cancer Treatment Rep.* (June 1986) 70:715–720 discloses the relationship of glutathione depletion to the antimitotic properties of estramustine.

Russo et al., *Int. J. Radiat. Oncol. Biol. Phys.* (Aug. 1986) 12:1347–1354 discloses the roles of intracellular glutathione in antineoplastic chemotherapy.

Dorr et al., *Invest. New Drugs* (1986) 4:305–313 discloses the cytotoxic effects of glutathione synthesis inhibition by BSO on human and murine tumor cells.

Green et al. *Cancer Res.* (Nov. 1984) 44:5427–5431 discloses that incubation of cells in the presence of BSO resulted in markedly increased (synergistic) melphalan cytotoxicity, and Ozols, *Semin. Oncol.* (Sept. 1985) 12:7–11 discloses that BSO increases the cytotoxicity of melphalen and cisplatin.

Ozols et al., *Dev. Oncol.* (1986) 47:277–293 discloses the effect of BSO on the efficacy of antitumor drugs.

Crook et al., *Cancer Res.* (1986) 46:5035–5038 discloses that BSO enhances the cytotoxicity of cyclophosphamide. Hodgkiss et al., *Biochem. Pharmacol.* (1985) 34:2175–2178 discloses use of BSO to enhance the cytotoxicity of nitroaromatic compounds. Somfai-Relle et al., *Biochem. Pharmacol.* (1984) 33:485–490 discloses that BSO sensitizes murine tumor cells to L-phenylalanine mustard.

SUMMARY OF THE INVENTION

Accordingly, the present invention is based on the discovery that the therapeutic index of the lymphokine or cytotoxin can be enhanced in in vitro and in vivo systems by concomitantly or separately treating the host with a free radical scavenger such as a radiation protector or a metabolic inhibitor in amounts that increase the efficacy and/or decrease the toxicity of the lymphokine or cytotoxin.

More specifically, the present invention is directed to a method for therapeutic or prophylactic treatment of biological damage to mammalian hosts caused by free radical production which method comprises administering to the host pharmacologically effective amounts of at least one lymphokine or cytotoxin from a mammalian species and at least one biological modifier selected from a free radical scavenger or a metabolic inhibitor.

Preferably, the lymphokine or cytotoxin is tumor necrosis factor or interleukin-2 and the free radical scavenger or metabolic inhibitor is uric acid, buthionine sulphoximine, vitamin C, indomethacin, ibuprofen, N-acetyl cysteine, or aspirin.

In another aspect, the present invention provides a composition suitable for administration to mammalian hosts comprising a mixture, in pharmacologically effective amounts, of at least one lymphokine or cytotoxin from a mammalian species and at least one biological modifier as specified above.

Without intent to be limited to any one theory, it is believed that the sensitivity of damaged cells, such as tumorous, infected, or irradiated cells, to a lymphokine or cytotoxin such as TNF is dependent on free-radical scavenging capacity. It is also believed that activation of the arachidonic acid cascade may be involved in the mechanism or action of the lymphokine or cytotoxin, which can produce lipid peroxidation and other associated radical species, as well as the biologically active metabolites of the lipoxygenase and cyclooxygenase pathways.

DESCRIPTION OF THE PREFERRED EMBODIMENTS

As used herein, the term "lymphokine" refers to low molecular weight proteins that are secreted by T cells and/or microphages when antigens or lectins stimulate T cell or macrophage growth or activation. The term "cytotoxin" refers to any protein that activates effector cells that kill foreign agents such as pathogens in the cell. Examples of such lymphokines and cytotoxins include, but are not limited to, interferons (e.g., interferon-alpha, (IFN-$\alpha$), interferon-beta, (IFN-$\beta$), and interferon-gamma, (IFN-$\alpha$)), interleukins (e.g., interleukin-1 (IL-1), interleukin-2 (IL-2), interleukin-3 (IL-3), and interleukin-4 (IL-4)), tumor necrosis factor-alpha (TNF-$\alpha$), tumor necrosis factor-beta (TNF-$\beta$) (also called lymphotoxin), a colony stimulating factor (e.g. CSF-1, CSF-G or CSF-GM), chemotaxins, migration inhibitory activity factor (MIF), macrophage-activating factor (MAF), NK cell activating factor, T cell replacing factor, leukocyte-inhibitory factor (LIF), other lymphotoxins, osteoclast-activating factor (OAF), soluble immune response suppressor (SIRS), growth-stimulating factor, a monocyte growth factor, etc. Preferably, the lymphokine or cytotoxin is an interleukin (more preferably IL-2), an interferon (more preferably IFN-$\beta$), TNF-$\alpha$ or -$\beta$, or a colony stimulating factor (more preferably CSF-1). The most preferred herein is TNF-$\alpha$.

As used herein, the term "recombinant" refers to lymphokines or cytotoxins produced by recombinant DNA techniques wherein generally the gene coding for the lymphokine or cytotoxin is cloned by known recombinant DNA technology. For example, by using the human lymphokine or cytotoxin cDNA as a template, the gene showing complementarity to the human lymphokine or cytotoxin cDNA is inserted into a suitable DNA vector such as a bacterial plasmid, preferably an E. coli plasmid, to obtain a recombinant plasmid, and the plasmid is used to transform a suitable host. The gene is expressed in the host to produce the recombinant protein. Examples of suitable recombinant plasmids for this purpose include pBR322, pCR1, pMB9 and pSC1. The transformed host may be eukaryotic or prokaryotic, preferably, a prokaryotic host.

As used herein, the term "pharmaceutically acceptable" refers to a carrier medium which does not interfere with the effectiveness of the biological activity of the active ingredients and which is not toxic to the hosts to which it is administered.

As used herein, the term "prophylactic or therapeutic" treatment refers to administration to the host of the lymphokine(s) or cytotoxin(s) and biological modifiers(s) either before or after onset of the biological damage to the host. If the lymphokine(s) or cytotoxin(s) and biological modifier(s) are administered prior to exposure to the agent causing the biological damage, the treatment is prophylactic (i.e., it protects the host against the damage), whereas if it is administered after exposure to the agent causing the damage, the treatment is therapeutic (i.e., it alleviates the existing damage). The scheduling and dosing will depend, e.g., on the type of host, disease, lymphokine or cytotoxin, and biological modifier. If the biological damage is caused by infection, the doses are preferably administered from 18 hours before infection for prophylactic treatment and in early phase of infection for therapeutic treatment, up to 18 hours after infection in later phase of infection for therapeutic treatment.

If the biological damage is cancer, the treatment is not considered therapeutic if after treatment a tumor appears or if an existing tumor burden is not eliminated or decreased. The effect of the doses will diminish with time, but for humans the dose may be repeated for months or even years. Prophylactic treatment of cancer refers to administration after the patient has been treated for cancer, to prevent reoccurrence of the cancer.

As used herein, the term "biological damage to the host caused by free radical generation" refers to any cellular, tissue or other damage to body parts or functions sustained by the host as a result of free radicals being produced in the body of the host. The free radicals may cause directly mobilization of the arachidonic acid metabolic pathways or may cause lipid peroxidation that mobilizes arachidonic acid. These radicals may be produced as a mechanism for killing cells. Examples by which such damage may be caused include hyperthermia, which may occur during cancer treatment as when the temperature of the tumor is increased via local or general microwave irradiation, damage caused by chemotherapeutic agents (chemotherapy), radiation therapy, or high oxygen tension that produce radicals to kill cells, and infection. Also, treated tumor cells may help propagate radical damage. An example of high oxygen tension is the condition that occurs when premature babies are exposed to high pressure oxygen, resulting in retinal and lung disease. Other conditions that represent damage caused by free radical generation may also be envisioned and fall within this definition.

The term "cancer" as used in the above definition refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer and gastrointestinal or stomach cancer. Preferably, the cancer is colon cancer, melanoma, renal cell cancer, sarcoma, lung cancer, adenocarcinoma, or breast cancer.

The term "infection" as used in the above definition refers to any kind of pathogenic disease, including those caused by bacteria, fungi, viruses, protozoa or parasites. Examples of bacterial infections include P. aeruginosa, E. coli, tetanus, Mycobacterium species, Streptococcal strains, diphtheria and Salmonella. Examples of fungal infections include cryptococcosis, histoplasmosis, and other infections due to Candida species. Examples of viral infections include Hepatitis A, recurrent Herpes Simplex, AIDS, Herpes Zoster, influenza, and rhinoviruses. Preferably, the infection is bacterial, more preferably Gram-negative infection, and most preferably P. aeruginosa and E. coli infection.

As used herein, the term "biological modifier" refers to one of two compounds: a free radical scavenger or a metabolic inhibitor. The term "free radical scavenger" refers to any compound or substance that protects a mammalian host against biological damage caused by free radical generation. This definition includes those agents that act through direct radical scavenging as well as those that act by altering the radical scavenging ability of the host and/or tumor. Either mechanism will affect the response of the host to the lymphokine or cytotoxin. Such free radical scavengers may be radiation protectors, and include such compounds as, for example, uric acid, buthionine sulfoximine, diethyl maleate, vitamin E, vitamin C, cysteine such as N-acetyl cysteine, or glutathione, metronidazole, and a retinoid such as, e.g., vitamin A. While diethyl maleate may increase the toxicity of the lymphokine or cytotoxin, it also reduces glutathione preferentially in tumor versus host and therefore should lead to a higher therapeutic index. Any combination of these modifiers may be employed. Most preferably, the free radical scavenger employed herein for humans is buthionine sulphoximine, vitamin C, vitamin E, or N-acetyl cysteine (the latter having the tradename Mucomyst (Mead Johnson) ). See the 1987 Physicians' Desk reference, ed. 41, Barnhart, pub., Oradell, N.J.: Medical Economics Company, Inc. Uric acid causes gout in humans to it may be tolerated in lesser amounts; it occurs naturally in human plasma at about 300 µM; it is expected that about 600–1500 µM might be tolerated in humans.

The second type of biological modifier, a "metabolic inhibitor," refers to a compound or substance that blocks or inhibits the cyclooxygenase and/or lipoxygenase metabolic pathways, of the arachidonic acid cascade, wherein phospholipids are converted to arachidonic acid, by phospholipase A2 or C, and the arachidonic acid may proceed by either metabolic pathway. Such blockage or inhibition may be of an enzyme that catalyzes one or both pathways, of a cell type that contains the enzyme, or of one or more of the natural products of the pathways. Reduction in the number of those leukotrienes, hydroperoxy-eicosatetraenoic acid, hydroxy- and dihydroxy-eicosatetraenoic acids, prostaglandins, thromboxanes, and/or prostacyclins that lead to biological damage as defined herein indicates metabolic inhibition.

Examples of metabolic inhibitors include aspirin, indomethacin, ibuprofen, nordihydroguaiaretic acid (4,4'-[2, 3-dimethyl-1,4-butanediyl]-bis[1,2-benzenediol]) (NDGA), cis-8,11,14-eicosatrien-5-ynoic acid (ETYA), and synthetic (as opposed to natural) prostaglandins and/or leukotrienes that block the effects of the natural metabolic products at the production level rather than at the enzyme level. Aspirin, indomethacin, ibuprofen, and ETYA block the cyclooxygenase pathway, thereby inhibiting the production of natural prostaglandins, thromboxanes and prostacyclins. At higher concentrations, indomethacin also block phospholipase $A_2$. NDGA and ETYA block the lipoxygenase pathway, thereby inhibiting the production of natural hydroperoxy-eicosatetraenoic acid, leukotrienes, and hydroxy- and dihydroxy-eicosatetraenoic acids. The preferred metabolic inhibitors herein for use with TNF and those selected from aspirin, indomethacin, and ibuprofen. Indomethacin is a non-steroidal antirheumatic agent with local antiinflammatory activity and is available from such manufacturers as Lederle Labs. Ibuprofen is a substitute for aspirin and is also available from Lederle Labs. Both drugs are referred to in the 1987 *Physician's Desk Reference*, supra.

As used herein, the term "pharmacologically effective amounts" as applied to the lymphokine or cytotoxin and the biological modifier refers to the amount of each component in the mixture or administered to the host that results in an increase in the therapeutic index of the host. The "therapeutic index" can be defined for purposes herein in terms of efficacy (extent of tumor or infection reduction or other cure) and in terms of toxicity to the host.

For non-human hosts, if the efficacy increases at least 50% over the efficacy using an excipient control (e.g., phosphate buffered saline) and the ratio of mean body weight at the end of the evaluation period for efficacy response to mean body weight at the start of treatment is at least 0.90 (i.e., no greater than 10% body weight loss), the therapeutic index has increased. The ratio of mean body weights indicates the extent of toxicity, with a value of 1 indicating no toxicity. For non-human hosts being treated for cancer, the extent of efficacy achieved may be measured by the ratio of mean tumor volume at the end of the evaluation period for efficacy response to mean tumor volume at the start of treatment. A reduction in the ratio of at least 50% of treated over excipient control indicates increased efficacy. The most preferred doses, schedules, and types of biological modifiers are those that achieve a mean tumor volume ratio of between 0 and 5, with a value of 0 being optimum and indicating a cure.

For human hosts, if the efficacy increases at least 50% upon treatment with the lymphokine/cytotoxin and biological modifiers and the toxicity is acceptable, i.e., no more than fever, chills, and/or general malaise, the therapeutic index has increased. For human hosts being treated for cancer, the extent of efficacy is generally ascertained in the clinic by measuring the perpendicular diameters of the products of all measured disease. A partial response occurs when the tumor shrinks by at least 50% in the sum of the products of the perpendicular diameters of all measured disease. For example, if a tumor having perpendicular diameters of 10 and 10 shrinks to perpendicular diameters of 8 and 8, the tumor has only shrunk from 100 to 64, which is not a 50% reduction and is not a partial response. If the tumor of 10 and 10 shrinks to 7 and 7, however, this is a partial response because it has shrunk from 100 to 49, more than 50%.

The method of this invention involves administering to a mammalian host, preferably a human host, pharmacologically effective amounts of one or more lymphokines or cytotoxins and one or more biological modifiers. The lymphokine(s), cytotoxin(s) and biological modifier(s) may be combined in vitro before administration or separately administered to the host, in either order or concurrently or simultaneously, with any administration of lymphokine/cytotoxin generally taking place up to 24 hours after the administration of biological modifier, and with any administration of biological modifier taking place up to about one hour after the administration of lymphokine/cytotoxin. Preferably the biological modifier is added prior to adding or concurrently with the lymphokine or cytotoxin.

The administration(s) may take place by any suitable technique, including oral, subcutaneous and parenteral administration, preferably parenteral or oral. Examples of parenteral administration include intravenous, intraarterial, intramuscular, and intraperitoneal, with intraperitoneal and intravenous being preferred.

The dose and dosage regimen will depend mainly on whether the lymphokine(s) or cytotoxin(s) and biological modifier(s) are being administered for therapeutic or prophylactic purposes, separately or as a mixture, the type of biological damage and host, the history of the host, the type of lymphokine or cytotoxin, and the type of biological modifier employed. The amount must be effective to achieve an enhanced therapeutic index as defined above. It is noted that humans are treated longer than the mice and rats exemplified herein which treatment has a length proportional to the length of the disease process and drug effectiveness. The doses may be single doses or multiple doses over a period of several days, but single doses are preferred. For purposes herein, a protection level of at least 50% means that at least 50% of the treated hosts exhibit improvement against the infection, including but not limited to improved survival rate, more rapid recovery, or improvement or elimination of symptoms.

Generally, for cancer, the dosage amount must be effective to achieve some tumor reduction or augmentation of lymphokine-activated killer (LAK) cell activity. LAK cells are lymphoid cells that can lyse fresh, noncultured, natural-killer-cell-resistant tumor cells but not normal cells. The doses may be single doses or multiple doses. If multiple doses are employed, as preferred, the frequency of administration will depend, for example, on the type of host and type of cancer, dosage amounts, etc. For some types of cancers or cancer lines, daily administration may be effective, whereas for others, administration every other day or every third day may be effective, but daily administration ineffective. The practitioner will be able to ascertain upon routine experimentation which route of administration and frequency of administration are most effective in any particular case.

The dosage amounts for cancer which appear to be most effective herein are those that result in regression in size of the tumor or complete disappearance of non-reappearance of the tumor, and are not toxic or are acceptably toxic to the host patient. Generally, such conditions as fever, chills and general malaise are considered acceptable. In addition, the dose of biological modifier cannot be so large as to inhibit the anti-tumor activity of the lymphokine or cytotoxin. These optimum dose levels will depend on many factors, for example, on the type of host, cancer, route, schedule and sequence of administration, existing tumor burden, the type of lymphokine or cytotoxin and biological modifier, and the definition of toxicity. Toxicity may be defined by the extent and type of side effects in human hosts, with fever, chills and general malaise considered acceptable toxicity for the study herein, or by the amount of body weight loss or by death in non-human hosts after a certain period of time, as defined above for the therapeutic index.

If TNF-α is employed as the lymphokine or cytotoxin, the dosage level thereof in humans is generally at least 0.24 µg/kg patient weight, and in mice is at least 25 µg/kg. As a general rule, the amount of TNF-α administered to humans is the approximate or exact number that is used for mice, but the units are µg/m$^2$ rather than µg/kg. Preferably, TNF-α is administered to humans in an amount of about 25 to 100 µg/m$^2$ when buthionine sulphoximime is administered in a minimum effective radical scavenging concentration before and/or during the course of administration of the TNF-α. Smith et al., *Proceedings of AACR*, 28 (March 1987), p. 440 discloses that in beagle dogs fifteen doses of 100 mg/kg/dose of BSO orally every eight hours is relatively non-toxic, whereas 400–800 mg/kg of BSO is toxic under those conditions of administration. Preferably, TNF-α is administered to humans in an amount of 125 µg/m$^2$ when vitamin C is administered in a minimum effective radical scavenging concentration prior to administration of the TNF-α. Preferably, TNF-α is administered to humans in an amount of 25–100 µg per m$^2$ when aspirin is administered in an amount of about 15–30 mg/kg of patient weight prior (e.g., 1–4 hours) to administration of TNF-α. Preferably, TNF-α is administered to humans in an amount of about 50–200 µg/m$^2$ when indomethacin is administered in an amount of about 25–50 mg prior to administration of the TNF-α. Preferably, TNF-α is administered to humans in an amount of about 150–250 µg/m$^2$ host when ibuprofen is administered in an amount of about 400 to 600 mg, when ibuprofen is administered prior to administration of TNF-α. Preferably, TNF-α is administered to humans in an amount of about 200–400 µg/m$^2$ when N-acetyl cysteine is administered in an amount equivalent to 250–1000 mg/kg of rat weight prior to the administration of TNF-α. The practitioner will be able to determine optimum dosage levels and scheduling when the host, lymphokine/cytotoxin and biological modifier are varied.

If IL-2 is employed as the lymphokine or cytokine, the dosage level thereof in humans is generally at least about $3 \times 10^6$ units/m$^2$/day and in mice is at least about 5–10 mg/kg. Preferably, the IL-2 is administered to humans in an amount of at least $3 \times 10^6$ units/m$^2$/day when vitamin C, vitamin E, aspirin, N-acetyl cysteine, ibuprofen or indomethacin is administered prior to administration of the IL-2.

The dosage level of CSF-1 in humans has not yet been determined, but in mice it may generally be about 50 mg/kg (at 100–150 mg/kg the mice being to die).

The typical dosage level of interferon (especially INF-β) in humans ranges from about 100 units to one billion units/m$^2$. Preferably, IFN-β is administered to humans in an amount of at least 1000 units/m$^2$ when vitamin C, vitamin E, aspirin, N-acetyl cysteine, ibuprofen, or indomethacin is administered prior to administration of the IFN-β.

For parenteral administration the lymphokine(s) will generally be formulated in a unit dosage injectable form (solution, suspension, emulsion), preferably in a pharmaceutically acceptable carrier medium which is inherently non-toxic and non-therapeutic or non-prophylactic. Examples of such vehicles include water, saline, Ringer's solution, dextrose solution, mannitol, and normal serum albumin. Non-aqueous vehicles such as fixed oils, propylene glycol and ethyl oleate may also be used. The carrier medium may contain minor amount of additives such as substances that enhance isotonicity and chemical stability, e.g., buffers and preservatives. The lymphokine(s)/cytotoxins and biological modifiers will typically be formulated in such carriers at a concentration of about 0.1 mg/ml to 100 mg/ml of each, preferably 0.2 to 1 mg/ml of each.

Alternative, if the lymphokine is IL-2, it may be made into a sterile, stable lyophilized formulation in which the purified IL-2 is admixed with a water-soluble carrier such as mannitol, which provides bulk, and a sufficient amount of sodium dodecyl sulfate to ensure the solubility of the recombinant IL-2 in water. The formulation is suitable for reconstitution in aqueous injections for parenteral administration and it is stable and well-tolerated in human patients. The formulation method is more completely described in U.S. Pat. No. 4,604,377, the disclosure of which is incorporated herein by reference. Alternatively, the IL-2 may be refolded using guanidine to obtain a more soluble product. Guanidine may be used to solubilize the IL-2 particle paste, as described in copending U.S. Ser. No. 048,408 filed May 11, 1987, the disclosure of which is incorporated herein by reference, incorporating the steps of:

(a) disrupting the cell membrane of the microorganism;

(b) separating water-insoluble, IL-2-containing material from the disruptate;

(c) mixing the insoluble IL-2-containing material of step (b) at a pH of about 7 to about 9 with an aqueous solution of a reducing agent and a chaotropic agent whereby the IL-2 in the insoluble material is dissolved and denatured;

(d) separating the IL-2-containing solution of step (c) from the undissolved portion of the insoluble material;

(e) removing the reducing agent from the separated IL-2-containing solution;

(f) oxidizing the IL-2 in the solution while maintaining the concentration of chaotropic agent at a strongly denaturing concentration, whereby the natural disulfide bridge of IL-2 is formed;

(g) after the oxidation of step (f) is complete, diluting the solution to reduce the concentration of chaotropic agent in the solution to a level at which the oxidized IL-2 is permitted to renature and a precipitate forms;

(h) separating the precipitate from the solution to provide a supernatant;

(i) purifying the oxidized IL-2 in the supernatant by (1) reverse-phase high performance liquid chromatography followed by dissolution of the precipitate resulting from the chromatography in a solution of chaotropic agent and removal of the chaotropic agent from the solution, or (2) hydrophobic interaction chromatography followed by ion exchange chromatography; and (j) recovering a purified oxidized, soluble, heterologous human IL-2 composition having an IL-2 content of at least about 95% as determined by reducing sodium dodecyl sulfate polyacrylamide gel electrophoresis analysis, a solubility in phosphate buffered saline of at least about 5 mg IL-2 per ml, a specific activity of at least about $1\times10^6$ units/mg as determined by HT-2 cell proliferation assay, and an endotoxin content of less than about 0.1 nanograms per mg of IL-2.

In another embodiment, the guanidine may be used after the HPLC step, as described in copending U.S. Ser. No. 048,405 filed May 11, 1987, the disclosure of which is incorporated herein by reference. Briefly, the rIL-2 is separated from the bulk of the cellular components of the transformed microorganism hosts containing the rIL-2, the rIL-2 is solubilized in a reduced form, oxidized, purified to clinically acceptable purity and endotoxin levels, and denatured by placing the rIL-2 in a solution of a chaotropic agent. Thereafter, the solids are removed from the solution and the rIL-2 is renatured from the solution. Preferably, the solution of a chaotropic agent is a 4 to 8M aqueous guanidine hydrochloride solution.

In yet another alternative, the IL-2 may be administered in an adoptive immunotherapy method, together with isolated, lymphokine-activated lymphocytes, in a pharmaceutically acceptable carrier, where the lymphocytes have antitumor activity when administered with the IL-2 to humans suffering from the tumor. This method is described more fully in U.S. Pat. No. 4,690,915 issued Sep. 1, 1987, and by S. Rosenberg et al., *New England Journal of Medicine* (1985), 313:1485–1492, the disclosures of which are incorporated herein by reference. In another alternative, described in S. Rosenberg et al., *Science*, 233:1318–1321 (1986), tumor-infiltrating lymphocytes (TIL) expanded in IL-2 may be adoptively transferred for the therapeutic treatment, particularly in combination with cyclophosphamide. The TIL approach of Rosenberg et al., the disclosure of which is incorporated herein by reference, may also be used herein.

As mentioned above, the recombinant lymphokine employed herein may be any lymphokine, obtained from tissue cultures or by recombinant techniques, and from any mammalian source such as, e.g., mouse, rat, rabbit, primate, pig, and human. Preferably the lymphokine is derived from a human source and more preferably is a human recombinant lymphokine. Most preferably the lymphokine is recombinant human IL-2 or TNF alone or in combination with recombinant TNF or IL-2, respectively.

The recombinant IL-2 may be obtained as described by Taniguchi et al., *Nature*, 302:305–310 (1983) and Devos, *Nucleic Acids Research*, 11:4307–4323 (1983) by cloning the native human IL-2 gene and expressing it in transformed microorganisms. It may also be an IL-2 mutein as described in U.S. Pat. No. 4,518,584, in which the cysteine normally occurring at position 125 of the wild-type or native molecule has been replaced by a neutral amino acid such as serine or alanine, or an IL-2 mutein as described in copending U.S. application Ser. No. 810,656 filed Dec. 17, 1985, the disclosure of which is incorporated herein by reference, in which the methionine normally occurring at position 104 of the wild-type or native molecule has been replaced by a neutral amino acid such as alanine.

Preferably, the IL-2 is an unglycosylated protein which is produced by a microorganism which has been transformed with the human cDNA sequence or a modified human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (deletions, additions, substitutions) which do not cause an adverse functional dissimilarity between the synthetic protein and native human IL-2. Examples of IL-2 proteins with such properties include those described by Taniguchi et al., *Nature* (1983), 302:305–310; Devos, *Nucleic Acids Research* (1983), 11:4307–4323; and by European Patent Publication Nos. 91,539 and 88,195; in U.S. Pat. No. 4,518,584, supra, and in copending U.S. application Ser. No. 810,656 filed Dec. 17, 1985, supra. Most preferably, the IL-2 is the des-ala$_1$-IL-2$_{ser125}$ mutein in which the initial terminal alanine is deleted and the cysteine at position 125 is replaced by a serine residue.

The IL-2 may be produced and purified to clinical purity by the method described and claimed in U.S. Pat. No. 4,569,790, issued Feb. 11, 1986, the disclosure of which is incorporated herein by reference. In addition, the IL-2 may be recovered from refractile bodies using sucrose as described in European Patent Publication No. 206,828 published Dec. 30, 1986, the disclosure of which is incorporated herein by reference. The IL-2 may also be modified by derivatization with polyethylene glycol or a polyoxyethylated polyol, as described in PCT 87/00056 published Jan. 15, 1987, the disclosure of which is incorporated herein by reference.

The human TNF-α herein may be obtained in recombinant form as described by Pennica et al., *Nature* (1984) 312:724–729; Yamada et al., *J. Biotechnology*, (1985) 3:141–153; Wang et al., *Science*, (1985) 228:149–154; Shirai et al., *Nature* (London), (1985) 313:803–806; EP 155,549 published Sep. 29, 1985; EP 158,286 published Oct. 16, 1985; EP 168,214 published Jan. 15, 1986; and PCT US85/01921 published Apr. 24, 1986. Recombinant rabbit TNF-α may be obtained as described in EP 146,026 published Jun. 26, 1985 and EP 148,311 published Jul. 17, 1985.

The cloning of human TNF-α having 151 and 155 amino acids (2 and 6 less than the native form) is disclosed in EP 155,549, published Sep. 25, 1985 (Dainippon Pharmaceutical Co., Ltd.), and human TNF-α having 155 amino acids is disclosed in EP 158,286, published Oct. 16, 1985 (Asahi Kasei Kogyo Kabushiki Kaisha) and corresponding GB 2,158,829A, published Nov. 20, 1985. The cloning of mature TNF-α (157 amino acids) and various modified forms (muteins) thereof is disclosed in EP 168,214, published Jan. 15, 1986 (Genentech), and U.S. Pat. Nos. 4,677,064, issued Jun. 30, 1987 and 4,677,063 issued Jun. 30, 1987 (both Cetus Corporation).

Preferably, the TNF-α herein is a human TNF mutein wherein one or more of the first eight amino acid residues, preferably either the first four or the first eight, have been deleted, using the procedure described in U.S. Pat. No. 4,677,064, supra, or the TNF-α is a cysteine-depleted mutein described in U.S. Pat. No. 4,677,063 issued Jun. 30, 1987, supra, and U.S. Pat. No. 4,518,584, supra. The TNF may be purified by the method described in European Patent Publication No. 220,966 published May 6, 1987, the disclosure of which is incorporated herein by reference.

The precise chemical structure of the TNF-α herein will depend on a number of factors. As ionizable amino and carboxyl groups are present in the molecule, a particular form of TNF-α may be obtained as an acidic or basic salt, or in neutral form. All such preparations which retain their bioactivity when placed in suitable environmental conditions are included in the definition of the TNF-α herein. Further, the primary amino acid sequence of the TNF-α may be augmented by derivatization using sugar moieties (glycosylation) or by other supplementary molecules such as lipids, phosphate, acetyl groups and the like, ore commonly by conjugation with saccharides. Certain aspects of such augmentation are accomplished through post-translational processing systems of the producing host; other such modifications may be introduced in vitro. In any event, such modifications are included in the definition of TNF-α herein so long as the bioactivity of the TNF-α is not destroyed. It is expected, of course, that such modifications may quantitatively or qualitatively affect the bioactivity by either enhancing or diminishing the activity of the TNF-α in the various assays.

In one formulation, described in copending U.S. Ser. No. 868,766 filed May 29, 1986, the disclosure of which is incorporated herein by reference, the TNF-α may be reacted with a homopolymer or copolymer of polyethylene glycol or a polyoxyethylated polyol, provided that the polymer is soluble in water at room temperature. The polymer is reacted first with a coupling agent having terminal groups reactive with both the free amino or thiol groups of the protein and the hydroxyl group of the polymer. Examples of such coupling agents include hydroxynitrobenzene sulfonic ester, cyanuric acid chloride and N-hydroxysuccinimide. The TNF-α is then formulated directly with the water-soluble carrier and buffer as described above, and the formulation may be lyophilized and the lyophilized mixture reconstituted as described above.

Recombinant IFN-γ may be obtained as described by Gray et al., *Nature*, 295:503 (1982).

The various aspects of the invention are further described by the following examples, which are not intended to limit the invention in any manner. In these examples all parts for solids are by weight and all percentages for liquids and gases are by volume, unless otherwise noted, and all temperatures are given in degrees Celsius.

EXAMPLE 1—Use of Uric Acid

A. General Treatment

Mice

Female Balb/c mice (Charles River Breeding Laboratories, Inc., Wilmington, Mass.) that were all 6–8 weeks old were employed in the in vivo tests. Animals are weight matched at 20±3 g, randomized at five per cage, and ear-notched. All animals were held in quarantine observation for seven days after arrival, maintained in microisolator cages (Lab Products, Inc.), and fed standard laboratory diets and drinking water ad lib.

TNF-α

A mutein of human TNF-α having the first eight amino acids deleted from the N-terminus was prepared as described in U.S. Pat. No. 4,677,064, issued Jun. 30, 1987 and Wang et al., *Science* (1985) 228:149–153, the disclosures of which are incorporated herein by reference. Briefly, TNF was induced from HL-60 cells and purified and sequenced. Then an intronless sequence encoding human TNF was prepared by producing enriched mRNA, constructing a cDNA library, selecting a probe and probing the library to recover the sequence. Then an ATG start codon was introduced immediately preceding the GTC sequence encoding N-terminal valine of the mature protein by site-directed mutagenesis. Clones were selected and strands ligated into expression vectors to obtain prokaryotic expression of the mutein. The mutein was then purified by column purification using any standard purification technique and recovered in the purification buffer. The mutein was produced as a lyophilized powder in sterile vials, reconstituted and suspended using sterile phosphate buffered saline within four days prior to use, and stored, if at all, at 4° C. The TNF contained less than 0.001 to 0.006 ng endotoxin/mg protein depending on production lot.

Free Radical Scavenger

The free radical scavenger employed herein was commercially available uric acid. (Sigma).

Cancer Cell Line and Tumor Injections

The target cells employed were a methylcholanthrene-induced murine fibrosarcoma (Meth-A) (Balb/c) obtained as an ascites-passed tumor from Dr. Lloyd Old, Memorial Sloan-Kettering Cancer Center, New York, N.Y., frozen as stock, and passed at least twice in ascites prior to use. These cells were implanted subcutaneously in the suprascapular area of the mouse host.

B. Results

Table I indicates the results obtained when the TNF mutein alone, uric acid alone, and various combination injections of the TNF mutein and uric acid were administered intravenously to five mice per group (2–3 repeats) beginning seven days after tumor implantation and every third day three times, with final measurements made on the 14th day. The excipient control was injected with PBS.

The uric acid dose was slightly below the maximum concentration attainable without decreasing animal weight, determined in a preliminary toxicity study, and was given immediately prior to the TNF inoculation.

The TNF doses were chosen to cover the ranges of 50, 100, 150, 200 and 250 µg/kg of mice weight (the mice weighing approximately 20 g each). The uric acid doses were 25 mg/kg of mouse weight whenever uric acid was administered.

TABLE I

| Group | ΔBW[a] | Deaths | ΔTW[b] | Cures |
|---|---|---|---|---|
| Excipient controls | 1.36 ± .13 | 1/15* | 60.4 ± 23.9 | 0/14 |
| Uric acid | 1.29 ± .07 | 1/15* | 51.7 ± 17.7 | 0/14 |
| TMF (50 µg/kg) | 1.1 ± .14 | 1/15 | 7.9 ± 6.2 | 1/14 |
| TNF (50 µg/kg) + | 1.05 ± .02 | 1/15* | 10.5 ± 5.9 | 0/14 |

TABLE I-continued

| Group | ΔBW[a] | Deaths | ΔTW[b] | Cures |
|---|---|---|---|---|
| uric acid | | | | |
| TNF (100 μg/kg) | 1.0 ± .02 | 1/10 | 1.4 ± 0.6 | 0/9 |
| TNF (100 μg/kg) + uric acid | 1.07 ± .12 | 1/10* | 16.4 ± 22 | 0/9 |
| TNF (150 μg/kg) | 1.04 | 6/10 | 0.42 | 0/4 |
| TNF (150 μg/kg) + uric acid | 1.02 ± .07 | 1/10* | 8.7 ± 7.3 | 0/9 |
| TNF (200 μg/kg) | 1.01 ± .03 | 5/10 | 0.48 | 3/5 |
| TNF (200 μg/kg) + uric acid | 1.04 ± .02 | 3/10 | 10.6 ± 3.1 | 0/7 |
| TNF (250 μg/kg) | — | 15/15 | — | — |
| TNF (250 μg/kg) + uric acid | 1.05 ± .07 | 8/15 | 1.21 ± 0.5 | 0/7 |

[a]ΔBW = change in body weight as measured by the ratio of mean body weight (in g) at 14 days after treatment to mean body weight (in g) at the start of treatment.
[b]ΔTW = change in tumor volumes as measured by the ratio of mean tumor volume (in mm³) at 14 days after treatment to mean tumor volume (in mm³) at the start of treatment.
[c]Cures = ΔTW = 0, or no visible tumor after 21 days from start of treatment.
* = "Tumor death", not toxic death.

The results show that combined treatment of the mice resulted in a decrease in toxicity over both PBS control and TNF alone as measured by host death, and in increase in efficacy as measured by comparing the ΔTW of the PBS control and the ΔTW of the combinations. Therefore, the therapeutic index as defined herein has been enhanced.

Uric acid has been postulated by Ames et al., supra, as a major protective agent against damage by reactive oxygen species and lipid peroxidation present in primates, but not rodents. The results of these experiments indicate that reactive oxygen radicals and/or lipid peroxide-like products play a role in the mechanism of action of TNF.

The practitioner can predict that these results likely would apply to humans based on the expected correlation between the TNF dose-related anti-tumor effect in animals and humans. The preclinical response of TNF alone correlated with a clinical response of TNF to colon cancer.

EXAMPLE 2—Use of Vitamin C (Ascorbic Acid)

Female Balb/c mice were implemented subcutaneously with Meth-A tumor cells as described in Example 1.

Table II indicates the results obtained when either vitamin C or the TNF mutein of Example 1 alone, or various combinations of vitamin C immediately followed by the TNF mutein were administered intravenously to groups of 5 mice beginning seven days after tumor implantation and continuing every third day for three injections, with measurements taken on the fourteenth day following the initiation of treatment.

TABLE II

| TNF μg/kg | Vit. C mg/kg | % Control ΔBW[a] | Deaths | % Control ΔTW[b] | "Cures"[c] |
|---|---|---|---|---|---|
| 125 | 0 | 81 | 1/10 | 1.5 | 4/9 |
| 125 | 7 | 92 | 0/5 | — | 5/5 |
| 125 | 35 | 86 | 0/5 | 10.0 | 0/5 |
| 125 | 70 | 83 | 2/5 | 12.0 | 0/5 |
| 0 | 0 | 100 | 0/5 | 100 | 0/5 |
| 0 | 7 | 92 | 0/5 | 76 | 0/5 |
| 0 | 35 | 100 | 0/5 | 88 | 0/5 |
| 0 | 70 | 96 | 0/5 | 74 | 0/5 |

[a]ΔBW = change in body weight as measured by the ratio of mean body weight (in g) at 14 days after treatment to mean body weight (in g) at the start of treatment; % control is the normalized value relative to the control groups.
[b]ΔTW = change in tumor volumes as measured by the ratio of mean tumor volume (in mm³) at 14 days after treatment to mean tumor volume (in mm³) at the start of treatment; % control is the normalized value relative to the control groups.
[c]Cures = ΔTW = 0, or no visible tumor after 21 days from start of treatment.

Vitamin C functions as an aqueous compartment radical scavenger, as well as in collagen stability, etc.

The results indicate that treatment with vitamin C and TNF at 125 μg/kg TNF dose resulted in fewer cures and little alteration in toxicity, but enhancement of efficacy over the PBS control at the two higher vitamin C doses. At high doses of TNF (250 μg/kg), buffering with vitamin C was not possible. Vitamin C alone was non-toxic at the three doses tested. As rodents have endogenous ascorbic acid, there may be regulatory mechanisms that influence exogenous administration. However, vitamin C appears to improve the therapeutic index significantly at the 7 mg/kg dose.

EXAMPLE 3—Use of Buthionine Sulphoximine (BSO)

Female Balb/c mice were implanted subcutaneously with Meth-A tumor cells as described in Example 1. Treatment was initiated seven days after the implantation.

A protocol was employed wherein BSO or the TNF mutein of Example 1 alone, or BSO together with the TNF mutein, were administered. BSO was administered intraperitonally and TNF intravenously. The BSO was started 24 hours prior to TNF administration twice daily (6–8 hours between doses) for ten days and TNF was given with the second BSO dose every third day for three times. BSO excipient was used as a volume control in the TNF alone groups. PBS was used as a control. The protocol is illustrated below:

| (Days) | −1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | BSO | TNF BSO | BSO | BSO | TNF BSO | BSO | BSO | TNF BSO | BSO | BSO | | | | | | |

Table III illustrates the results of this study, with the headings defined in the footnotes to Table II. The numbers in parentheses indicate the results from a repeat of the experiment.

TABLE III

Inhibition of Glutathione Synthesis by Buthionine Sulphoximine Increased the Sensitivity of Meth A to TNF In Vivo[a]

| Treatment Group | ΔBW[b] | Deaths | ΔTW[c] | Cures[d] | Dose Modification Factor[e] |
|---|---|---|---|---|---|
| BSO (1.25 g/kg) | 1.19 | 0/10 | 29.8 | 0/10 | — |
| TNF (25 μg/kg) | 1.09 | 0/10 | 7.8 | 1/10 | — |
| TNF (25 μg/kg) + BSO | 1.03 | 0/10 | 1.8[f] | 0/10 | 4.3 |
| TNF (50 μg/kg) | 1.04 | 0/10 | 4.9 | 1/10 | — |
| TNF (50 μg/kg) + BSO | 0.98 | 0/10 | 1.1[f] | 8/10 | 4.4 |
| TNF (100 μg/kg) | 0.99 | 1/10 | 1.9 | 3/9 | — |
| TNF (100 μg/kg) + BSO | 0.99 | 1/10 | — | 9/9 | ∞ |
| Controls (saline) | 1.20 | 0/10 | 30.0 | 0/10 | — |

[a]Data are for two independent experiments: 5 mice/group
[b]mean values of two experiments
[c]mean values
[d]"Cures" indicates no palpable tumor on day 14
[e]"Dose modification factor" is the ratio of ΔTW of TNF alone/ΔTW of TNF + BSO
[f]Significantly different from TNF alone group by Quade rank analysis of variance (p set at 0.05)

The results of these experiments indicate that the pretreatment with BSO increased the therapeutic index of the TNF at all doses of TNF tried; it increased the anti-tumor efficacy of TNF with little increase in toxicity, as illustrated in the column headed "Dose Modification Factor." The data further support the hypothesis that the in vivo mechanism of efficacy, and to some degree the toxicity, is related to free-radical production. Tumor cell sensitivity/resistance depends on the ability of the tumor cells to protect themselves from free radical damage.

The following Table IV illustrates the sensitivity of various human cell lines to TNF and the relationship of TNF sensitivity to glutathione (GSH) content in the cells. BSO is used to reduce preferentially the GSH level of Meth-A as compared to the host, thereby depleting the radical scavenging capacity of the tumor. All cell lines mentioned below are available form the American Type Culture Collection (ATCC) in Rockville, Md.

TABLE IV

Intracellular Glutathione Levels Correlate With TNF Resistance In Vivo

| Tumor Line | μM Total Glutathione Equivalents/ 10⁶ cells | % Tumor Growth Inhibition[a] |
|---|---|---|
| PAN-D2 (mouse tumor) | 484 ± 90 | 0 |
| HT29 (human colon tumor) | 308 ± 131 | 9 |
| P815 (mouse tumor) | 305 ± 197 | 20 |
| P388 (mouse tumor) | 280 ± 150 | 15 |
| B-16 (mouse tumor) | 180 ± 56 | 60 |
| L1210 (mouse tumor) | 105 ± 37 | 74 |
| ME180 (human cervical carcinoma) | 14.5 ± 4.6 | ND[b] |
| L929 (mouse tumor) | 14.0 ± 0.7 | ND[b] |
| Meth A (mouse tumor) | 9.1 ± 4.3 | 100 |

[a]Determined at the maximum tolerated dose of TNF at an endpoint defined as the control tumor increasing in volume at least 20-fold; for these models generally 17–28 days post-implantation. For the L1210, P388, P815, and B-16 tumor lines, mice were treated daily for 14 days i.p., at 250 μg/kg, one day following subcutaneous tumor inoculation. PAN-02 and HT29 were treated every third day, three times, i.v., at 150 or 100 μg/kg, respectively, starting 7 days after tumor inoculation. These conditions resulted in less than 10% body weight loss vs. controls, and were considered to be the maximal anti-tumor efficacy signal obtainable in these models without inducing non-specific tumor growth inhibition due to host toxiciy.
[b]Not determined. Previously published data have shown that in vitro, the dose of TNF at which 50% of the animals die (TCID₅₀) for ME180 = 50 u/ml; L929 = 20 u/ml (Creasey et al., Canc. Res., 47:145–149 (1987)).

EXAMPLE 4—Use of Aspirin

Female Balb/c mice were treated by subcutaneous implantation of Meth-A tumor cells as described in Example 1. Five mice per group were employed. Treatment was initiated seven days after the implantation.

A protocol was employed wherein aspirin or the TNF mutein of Example 1 alone, or aspirin together with the TNF mutein, were administered intravenously. In the combination group, aspirin was administered daily for five days and each dose was followed 1–4 hours later by TNF. PBS was used as a control.

When 250 μg/kg TNF was administered after a single dose of 30 mg/kg aspirin or doses of aspirin once a day for five days, 9/10 aspirin-treated mice died with 48 hours of treatment with TNF. In contrast, aspirin alone was non-toxic, and TNF alone resulted in 1/5 mice dead.

The dosage of TNF was reduced to 25–150 μg/kg host weight, and the results are indicated in Table V, where final measurements were taken 14 days after treatment began. The headings are defined in the footnotes of Table I.

TABLE V

| Group | ΔBW | Deaths | ΔTW | "Cures" |
|---|---|---|---|---|
| Aspirin (30 mg/kg) | 1.34 | 0/5 | 66.6 | 0/5 |
| PBS | 1.25 | 0/5 | 54.2 | 0/5 |
| TNF (25 μg/kg) + aspirin (30 mg/kg) | 1.15 | 0/5 | 23.8 | 0/5 |
|  | 1.17 | 1/5 | 23.4 | 0/4 |
| TNF (50 μg/kg) + aspirin (30 mg/kg) | 1.15 | 0/5 | 11.3 | 1/5 |
|  | 1.12 | 0/4 | 6.9 | 3/4 |
| TNF (100 μg/kg) + aspirin (30 mg/kg) | 1.06 | 0/5 | 3.2 | 2/5 |
|  | 1.09 | 1/5 | 5.6 | 3/4 |
| TNF (150 μg/kg) + aspirin (30 mg/kg) | 0.98 | 0/5 | 1.5 | 0/5 |
|  | 1.10 | 3/5 | 0.7 | 1/2 |

The results indicate that at the lower TNF doses, pretreatment with aspirin enhanced the therapeutic index of TNF (increased efficacy at the expense of a slight toxicity increase). In fact, the increase in efficacy over TNF alone as measured by ΔTW was by a factor of about 2 at 50 μg/kg TNF in the presence of 30 mg/kg aspirin, and, further, 3 out of 4 cures were obtained in the combination group compared to 1 out of 5 with TNF alone. At the 100 μg/kg TNF level, a similar trend was seen, at 3 out of 4 cures were obtained in the combination group compared to 2 out of 5 cures in the TNF alone group. At 150 µg/kg, the aspirin combination was more toxic with little change in efficacy.

EXAMPLE 5—Use of Nordihydroguaiaretic Acid (NDGA), Aspirin, or the Combination with TNF Female Balb/c mice were treated by subcutaneous implantation of Meth-A tumor cells as described in Example 1.

Table VI indicates the results obtained when NDGA (from Sigma Chemical Co.), aspirin, the combination of NDGA and aspirin, the TNF mutein of Example 1 alone, and various combinations of NDGA and aspirin followed by the TNF mutein were administered to groups of 5 mice beginning seven days after tumor implantation and continuing every third day three times. Details of the protocols are in the footnotes of Table VI. PBS was used as a control. Results were evaluated 14 days after initiation of treatment. The headings are defined in the footnotes of Table I.

TABLE VI

| Group | ΔBW | ΔTW | Cures | Deaths |
|---|---|---|---|---|
| TNF[a] + | 1.04 | 2.0 | 0/5 | 0/5 |
| aspirin + | 1.08 | 3.6 | 0/5 | 0/5 |
| NDGA[c] + | 1.04 | 3.1 | 0/5 | 0/5 |
| aspirin + NDGA | 1.03 | 0.7 | 0/5 | 0/5 |
| Aspirin (30 mg/kg)[d] | 1.2 | 60.3 | 0/5 | 0/5 |
| NDGA (15.6 mg/kg)[e] | 1.3 | 50.8 | 0/5 | 0/5 (1 tumor death d. 14) |
| Aspirin (30 mg/kg) + NDGA (15.6 mg/kg)[f] | 1.4 | 47.8 | 0/5 | 1/5 (d. 5) |
| PBS | 1.3 | 50.4 | 0/5 | 0/5 |

[a] = 100 µg/kg i.v. every third day 3 times for all combinations.
[b] = 30 mg/kg i.v. one hour prior to each TNF administration.
[c] = 312 µg/20 g mouse (15.6 mg/kg) in propylene glycol i.p. 5 minutes prior to each TNF administration.
[d] = i.v. every third day 3 times.
[e] = i.p. every third day 3 times.
[f] = aspirin i.v. every third day 3 times; NDGA i.p. one hour after each aspirin administration NDGA is known to inhibit the 5'-lipoxygenase pathway, which would be expected to inhibit leukotriene synthesis and, thereby, the toxicities associated with their production in the host. In addition, NDGA may function in the radical scavenging role in some cases, which role would be expected also to reduce the toxicity of TNF. The exact mechanisms at work under the present conditions are not entirely known at this time, but evidence has been presented to suggest that either effect or both effects would be expected to reduce TNF toxicity.

EXAMPLE 6—Use of Indomethacin, Ibuprofen or Aspirin with TNF

Female Balb/c mice were treated by subcutaneous implantation of Meth-A tumor cells as described in Example 1.

Table VII indicates the results obtained when aspirin, indomethacin, ibuprofen, and TNF mutein of Example 1 alone, and either aspirin, indomethacin or ibuprofen followed in two hours by the TNF mutein were administered to groups of 10 mice and of five mice beginning seven days after tumor implantation. Details of the protocols are referenced in the footnotes of Table VII. Results were evaluated 14 days after initiation of treatment for TGI, and at least 21 days, usually 28 days, for cure data. TGI is tumor growth inhibition, calculated as the % ratio of the weight of the treated tumor at day 14 to the weight of the tumor at day 14 of the controls, subtracted from 100. (For example, if treated volume is 30 and control volume is 1200, the ratio is 2.5% and the % TGI is 97.5.) Cures are the same as defined in footnote c of Table I.

The results show the best dosage for mice of TNF for 3 mg/kg indomethacin to be about 50–200 µg/kg host weight (50–200 µg/m$^2$ for humans). The effects of ibuprofen in combination with TNF were approximately equal to those of aspirin in combination with TNF. The results confirm the best dose of TNF for 30 mg/kg host aspirin.

EXAMPLE 7—Use of N-Acetyl Cysteine with TNF

CD rats purchased from Charles River Labs were injected with either 200 or 400 µg/kg of the TNF mutein described above in Example 1 intravenously once at 0 hours. In addition, CD rats were injected intravenously 24 hours and one hour prior to TNF treatment iv at 0 hours with N-acetyl cysteine (Sigma) at 250 and 100 mg/kg host. The data shown in Table VIII are the deaths with 24 hours/total rats treated. It can be seen that the administration of the N-acetyl cysteine reduces the toxicity of the TNF at all doses tested.

TABLE VII

Effects of Cyclooxygenase Inhibitors on TNF Toxicity and Efficacy

| Dose Group | Toxic Deaths/ Total Treated | Percent Deaths | Day of Death | Percent TGI | Percent Cures/Survivors |
|---|---|---|---|---|---|
| TNF (50 µg/kg)[a] | 0/40 | 0 | — | 75 | 30 |
| +INDO[b] | 0/25 | 0 | — | 94 | 68 |
| +IBU[b'] | 2/25 | 8 | 10.5 (7–14) | 72 | 35 |
| +ASA[c] | 0/30 | 0 | — | 86.5 | 35 |
| TNF (100 µg/kg)[d] | 4/35 | 11.4 | 1.5 (1–6) | 91.6 | 65 |
| +INDO[b] | 1/25 | 4 | 1 | 95.3 | 92 |
| +IBU[b'] | 4/25 | 16 | 2 (1–4) | 87.7 | 62 |
| +ASA[e] | 2/25 | 8 | 1 | 93.3 | 60 |
| TNF (200 µg/kg)[d] | 26/35 | 74 | 1 (1–5) | 96 | 75 |
| +INDO[b] | 14/25 | 56 | 1 (1–4) | 99.5 | 91 |
| +IBU[b] | 21/25 | 84 | 1 (1–7) | 99 | 100 |

TABLE VII-continued

Effects of Cyclooxygenase Inhibitors on TNF Toxicity and Efficacy

| Dose Group | Toxic Deaths/ Total Treated | Percent Deaths | Day of Death | Percent TGI | Percent Cures/Survivors |
|---|---|---|---|---|---|
| +ASA[f] | 34/40 | 85 | 1 (1–6) | 96 | 67 |
| TNF (300 µg/kg)[a] | 33/40 | 82.5 | 1 (1–6) | 100 | 67 |
| +INDO[b] | 24/25 | 96 | 1 (1–4) | 100 | 100 |
| +IBU[b'] | 25/25 | 100 | 1 | — | — |
| +ASA[d] | 33/35 | 94.3 | 1 (1–5) | 95 | 100 |

[a]TNF administered intravenously every third day for three times; 6 expts., with 2 expts. at 10 mice/grp. and 4 expts. at 5/mice grp.
[b]Indomethacin (3 mg/kg) administered ip, 2 hours before TNF every third day for three times; 3 expts., with 2 expts. at 10 mice/grp., and 1 expt. at 5 mice/grp.
[b']Ibuprofen (20 mg/kg) administered ip, 2 hours before TNF every third day for three times.
[c]Aspirin (30 mg/kg) IV, 2 hours before TNF every third day for three times; 4 expts. with 2 expts. at 10 mice/grp. and 2 expts. at 5 mice/grp.
[d]5 Expts., with 2 expts. at 10 mice/grp. and 3 expts. at 5 mice/grp.
[e]3 Expts, with 2 expts. at 10 mice/grp. and 1 expt. at 5 mice/grp.
[f]6 Expts, with 2 at 10 mice/grp. and 4 expts. at 5 mice/grp.
Endotoxin (LAL's):
INDO = >0.12/<1.2 ng/ml (200 µl dosing volume)
IBU = <0.2 ng/ml
ASA = <0.01 ng/ml

TABLE VIII

| | Deaths Within 24 Hours/Total Rats Treated | | |
|---|---|---|---|
| | 0 mg/kg N-acetyl cysteine | 250 mg/kg N-acetyl cysteine | 1000 mg/kg N-acetyl cysteine |
| 200 µg/kg TNF | 9/10 | 4/10 | 0/10 |
| 400 µg/kg TNF | 8/10 | 4/10 | 0/10 |

The above effects are expected to be observed in lymphokines of cytotoxins other than TNF. For example, the biological modifiers may play a role in IL-2 mediated tumoricidal activity. There has been found a clear relationship between the amount of radical scavenging capacity of various tumor cells (total glutathione content) and their sensitivity to both TNF and IL-2. The following experiment illustrates that IL-2 may be as effective as TNF.

EXAMPLE 8—Use of Uric Acid with IL-2

Female Balb/c mice were implanted subcutaneously with Meth-A tumor cells as described in Example 1.

An IL-2 mutein, designated des-ala$_1$-IL2-$_{ser125}$ (with no alanine at position 1 of the mature IL-2 molecule and a serine at position 125 of the mature IL-2 molecule), was prepared by the method described in U.S. Pat. No. 4,518, 584, supra, isolated from refractile bodies in accordance with the procedure described in EP 206,828 published Dec. 30, 1986, and formulated as described in U.S. Pat. No. 4,604,377 in sodium dodecyl sulfate. The disclosures of all these references are incorporated herein by reference. The designation des-ala$_1$-IL-2$_{ser125}$ indicates that the initial alanine of the mature native IL-2 sequence is missing and that the cysteine residue at position 125 of the mature native IL-2 sequence has been substituted with a serine.

Table IX indicates the results obtained when the IL-2 mutein described herein alone, uric acid alone, and various combination injections of the IL-2 mutein and uric acid were administered intravenously to five mice per group (2–3 repeats) beginning seven days after tumor implantation and once daily for five days, with the uric acid being administered immediately prior to (about 10 minutes) the IL-2 administration when both were administered. Final measurements were made on day 14. The excipient control was injected with PBS. The uric acid doses were all 25 mg/kg of mice weight. The headings are defined in the footnotes of Table I.

TABLE IX

| Group | ΔBW | Deaths | ΔTW | Cures |
|---|---|---|---|---|
| Excipient controls | 1.18 | 0/5 | 30.5 | 0/5 |
| Uric acid | 1.29 | 0/5 | 42.3 | 0/5 |
| IL-2 (1.5 mg/kg) | 1.08 | 0/5 | 11.6 | 0/5 |
| IL-2 (1.5 mg/kg) + uric acid | 1.13 | 0/5 | 18.4 | 0/5 |
| IL-2 (5.0 mg/kg) | 1.07 | 0/5 | 3.9 | 0/5 |
| IL-2 (5.0 mg/kg) + uric acid | 1.11 | 0/5 | 8.1 | 0/5 |

The results show that combined treatment of the mice resulted in a decrease in toxicity over the IL-2 control; however, the IL-2 was about 2-fold less efficacious when given with uric acid. This decrease is similar in magnitude to what was observed with lower TNF doses and uric acid. It is predicted that longer treatments and an increase in the dose of IL-2 will result in cures of the tumor. The preferred biological modifiers for human use are aspirin, vitamin C, vitamin E, ibuprofen, indomethacin, and N-acetyl cysteine. For humans, IL-2 is typically administered at a level of $3 \times 10^6$ units/m$^2$ per day.

The present invention achieves the following goals: First, the ability of the host or tumor to scavenge radicals is reduced by the combination therapy, for example with BSO, thereby increasing the therapeutic index of the tumor over the host. Second, the biological damage at the host level caused by free radical production is blocked, e.g., by the plasma-mediated radical scavenger, uric acid. Third, the metabolism of the arachidonate cascade, which is influenced by and itself produces reactive radical species in the lipid and aqueous compartments, can be modulated to increase the therapeutic index of the lymphokine or cytotoxin. Effective amounts of the biological modifier can be determined for humans based on translations from mice data when human clinical trials are undertaken.

In summary, the present invention is seen to provide a combination of lymphokine or cytotoxin and biological modifier that results in an enhanced therapeutic index relative to the lymphokine or cytotoxin alone in a mammalian host.

Modifications of the above-described modes for carrying out the invention which are obvious to those skilled in the fields of molecular and clinical biology, pharmacology, and related fields are intended to be within the scope of the following claims.

What is claimed is:

1. A method for the therapeutic or prophylactic treatment of biological damage to a mammalian host, said damage caused by free radical generation, which method comprises administering to the host in need of such treatment therapeutically effective amounts of a colony stimulating factor from a mammalian species and at least one biological modifier selected from the group consisting of a free radical scavenger and a metabolic inhibitor.

2. The method of claim 1 wherein the colony stimulating factor and the biological modifier are administered separately to the host, and the biological modifier is administered first.

3. The method of claim 1 wherein the biological modifier is selected from the group consisting of uric acid, buthionine sulphoximine, vitamin E, vitamin C, N-acetyl cysteine, a retinoid, gluathione, metronidazole, aspirin, indomethacin, ibuprofen, nordihydroguaiaretic acid, cis-8,11,14-eicosatrien-5-ynoic acid, synthetic prostaglandins, synthetic leukotrienes, and combinations thereof.

4. The method of claim 1 wherein said biological modifier is administered to the host at least once prior to administration to the host of said colony stimulating factor.

5. The method of claim 1 wherein the colony stimulating factor is selected from the group consisting of colony stimulating factor-1 (CSF-1) and granulocyte-macrophage colony stimulating factor (CSF-GM).

6. The method of claim 5 wherein the colony stimulating factor is CSF-1.

7. The method of claim 1 wherein the host is human and the biological damage results from a cause selected from the group consisting of infection, high oxygen tension, radiation therapy, and chemotherapy.

8. The method of claim 1 wherein the biological modifier is a free radical scavenger.

9. The method of claim 8 wherein the biological damage caused by free radical generation is caused by free radicals produced as a mechanism for killing cells.

10. The method of claim 1 wherein the biological modifier is a metabolic inhibitor.

11. A composition comprising therapeutically effective amounts of a colony stimulating factor from a mammalian species and of a biological modifier selected from the group consisting of a free radical scavenger and a metabolic inhibitor.

12. The composition of claim 11 further comprising a pharmaceutically acceptable carrier medium.

13. The composition of claim 11 wherein the colony stimulating factor is selected from the group consisting of colony stimulating factor-1 (CSF-1) and granulocyte-macrophage colony stimulating factor (CSF-GM).

14. The composition of claim 13 wherein the colony stimulating factor is colony stimulating Factor-1.

15. The composition of claim 13 wherein the colony stimulating factor is CSF-GM.

16. The composition of claim 11 wherein the biological modifier is selected form the group consisting of uric acid, buthionine sulphoximine, vitamin E, vitamin C, N-acetyl cysteine, a retinoid, glutathione, metronidazole, aspirin, indomethacin, ibuprofen, nordihydroguaiaretic acid, cis-8,11,14-eicosatrien-5-ynoic acid, synthetic prostaglandins, synthetic leukotrienes, and combinations thereof.

17. The composition of claim 11 wherein the biological modifier is a free radical scavenger.

18. The composition of claim 11 wherein the biological modifier is a metabolic inhibitor.

19. A method for treating biological damage in a host in need of such treatment, wherein said damage is caused by free radical generation, which method comprises administering to the host a therapeutically effective amount of a biological modifier in a first pharmaceutically acceptable carrier, said biological modifier selected from the group consisting of a free radical scavenger and a metabolic inhibitor, and administering to the host a therapeutically effective amount of a colony stimulating factor in a second pharmaceutically acceptable carrier.

20. The method of claim 19 wherein the biological damage is cancer.

21. The method of claim 20 wherein the colony stimulating factor is selected from the group consisting of colony stimulating factor-1 (CSF-1) and granulocyte-macrophage colony stimulating factor (CSF-GM).

22. The method of claim 20 wherein the biological modifier is a free radical scavenger.

23. The method of claim 20 wherein the biological modifier is a metabolic inhibitor.

24. A unit dose comprising a first composition having a therapeutically effective amount of a colony stimulating factor from a mammalian species, and further comprising a second composition having a therapeutically effective amount of a biological modifier selected from the group consisting of a free radical scavenger and a metabolic inhibitor.

25. The unit dose of claim 24 wherein said first composition and said second composition are cooperatively combined but not in admixture.

26. The unit dose of claim 25 wherein the colony stimulating factor is selected from the group consisting of colony stimulating factor-1 (CSF-1) and granulocyte-macrophage colony stimulating factor (CSF-GM).

27. The unit dose of claim 26 wherein the biological modifier is a free radical scavenger.

28. The unit dose of claim 27 wherein the free radical scavenger is selected from the group consisting of uric acid, buthionine sulphoximine, N-acetyl cysteine, and vitamin C.

29. A kit comprising a therapeutically effective amount of a colony stimulating factor from a mammalian species in association with a therapeutically effective amount of a biological modifier selected from the group consisting of a free radical scavenger and a metabolic inhibitor, said kit facilitating separate administration to a host of said therapeutically effective amount of a colony stimulating factor and said therapeutically effective amount of a biological modifier.

30. The kit of claim 29 wherein the colony stimulating factor is selected from the group consisting of colony stimulating factor-1 (CSF-1) and granulocyte-macrophage colony stimulating factor (CSF-GM).

31. The kit of claim 30 wherein the biological modifier is a free radical scavenger.

32. The kit of claim 31 wherein the free radical scavenger is selected from the group consisting of uric acid, buthionine sulphoximine, N-acetyl cysteine, and vitamin C.

* * * * *